United States Patent [19]

Madocks et al.

[11] Patent Number: 4,949,927

[45] Date of Patent: Aug. 21, 1990

[54] ARTICULABLE COLUMN

[75] Inventors: John E. Madocks; Thomas M. Young, both of Oakland, Calif.

[73] Assignee: John Madocks, Oakland, Calif.

[21] Appl. No.: 422,595

[22] Filed: Oct. 17, 1989

[51] Int. Cl.⁵ .................................................. E04G 3/00
[52] U.S. Cl. ........................................ 248/276; 248/160; 403/55; 403/56
[58] Field of Search ................ 248/276, 160, 288.5; 403/55, 56

[56] References Cited

U.S. PATENT DOCUMENTS

| | | | |
|---|---|---|---|
| 599,543 | 2/1898 | Whitaker | 248/160 |
| 870,429 | 11/1907 | Grimler | 248/160 |
| 912,308 | 2/1909 | Grimler | 248/160 |
| 936,379 | 10/1909 | Stevens | 248/160 |
| 1,279,803 | 9/1918 | Watson | 248/160 |
| 2,510,198 | 6/1950 | Tesmer | 248/160 X |
| 3,096,962 | 7/1963 | Meijs | 248/276 |
| 3,168,274 | 2/1965 | Street | 248/276 X |
| 3,529,797 | 9/1970 | Street | 248/160 |
| 3,584,822 | 6/1971 | Oram | 248/160 |
| 4,225,258 | 9/1980 | Thompson | 403/56 |

Primary Examiner—David M. Purol

[57] ABSTRACT

Presented is a method and apparatus for incrementally varying the frictional forces along an articulable column having succesive joints formed of alternate ball and socket members. Friction is varied by varying the contact angle between said ball and socket members along the length of the column and by supplying a compressive force to said joints via a tensioned means throughout the column. The effect of varying the frictional forces along the column is to vary the stiffness of individual column joints creating a structural member which can be tailored to the load requirements of a specific application.

8 Claims, 3 Drawing Sheets

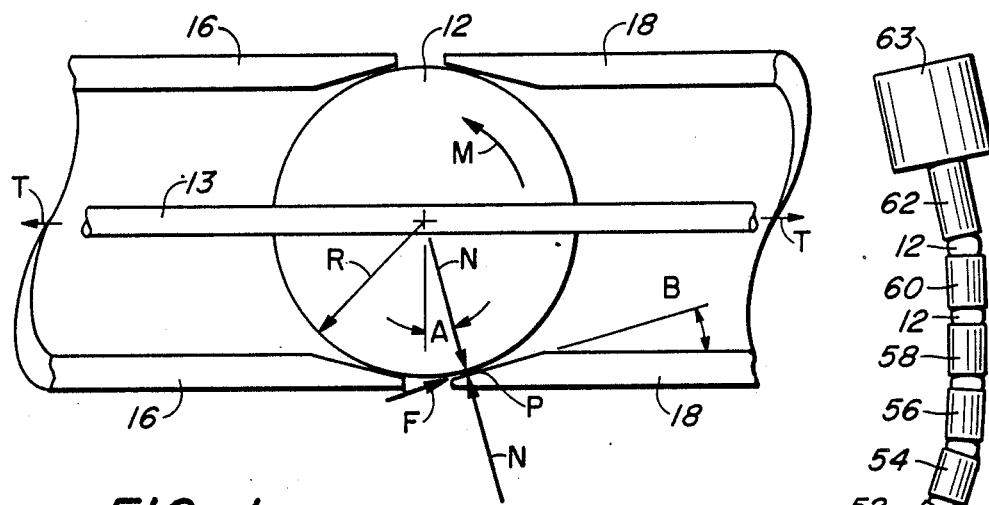
FIG._1.
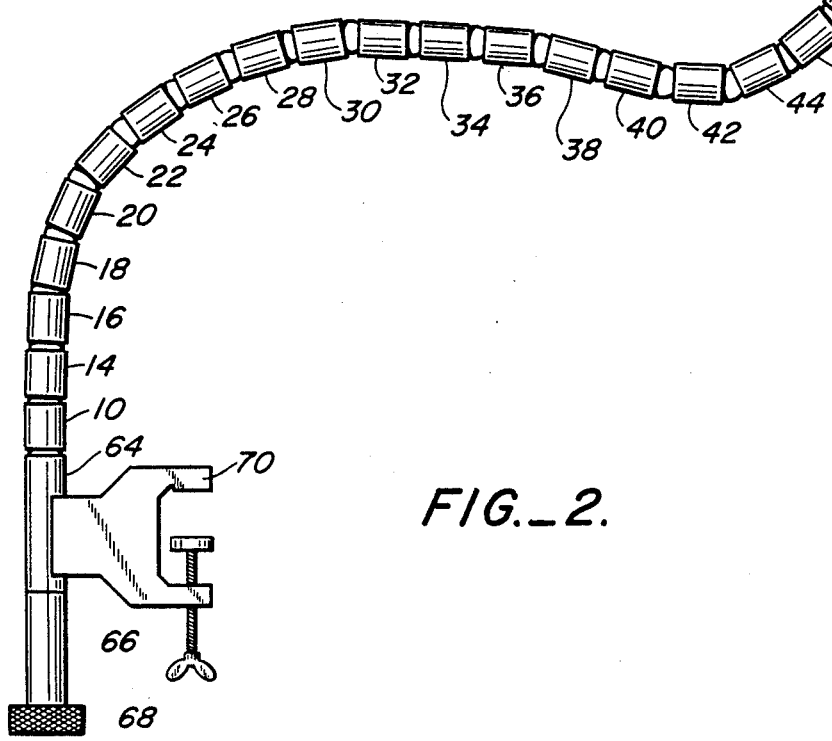
FIG._2.

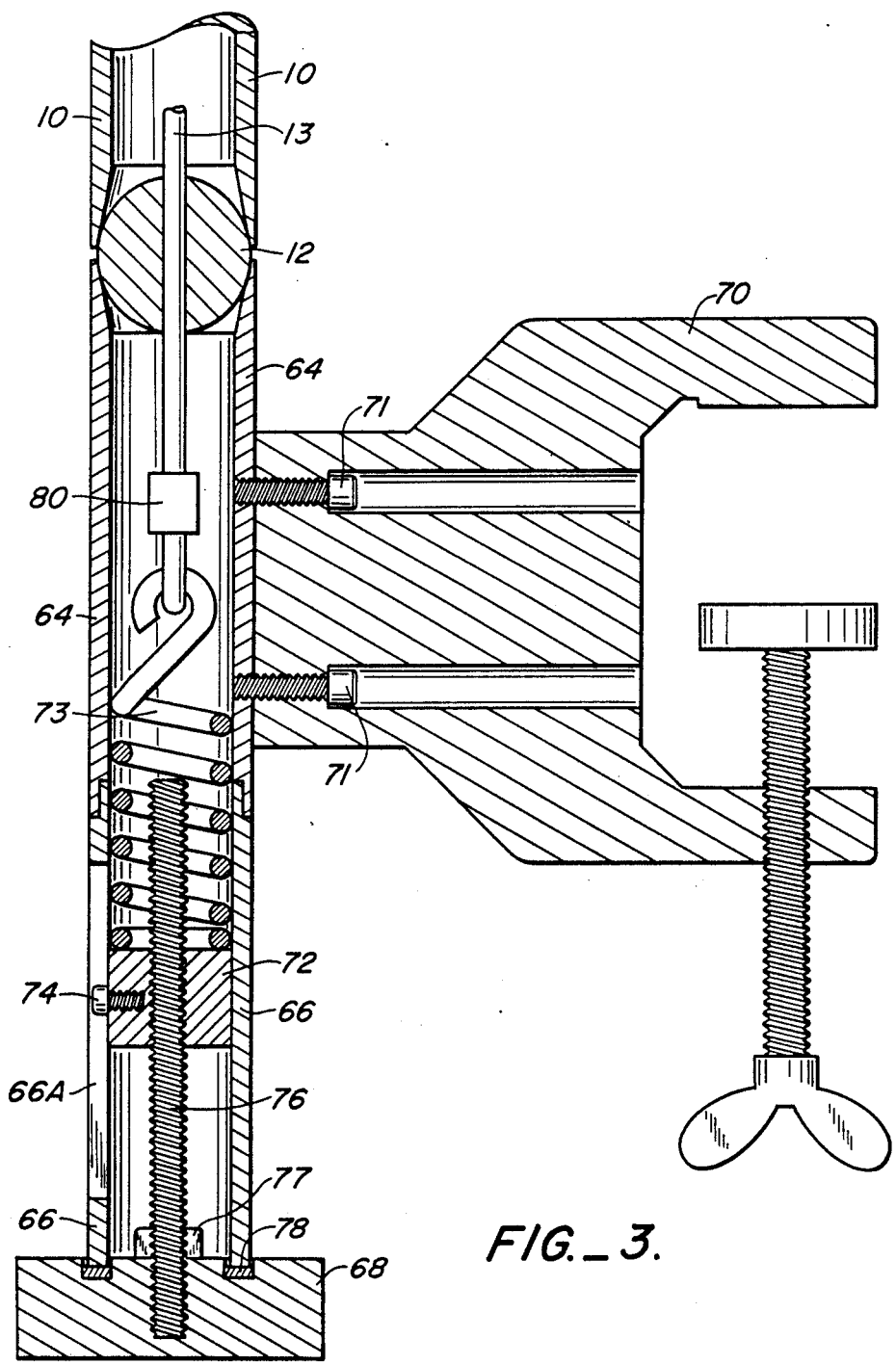
FIG._3.

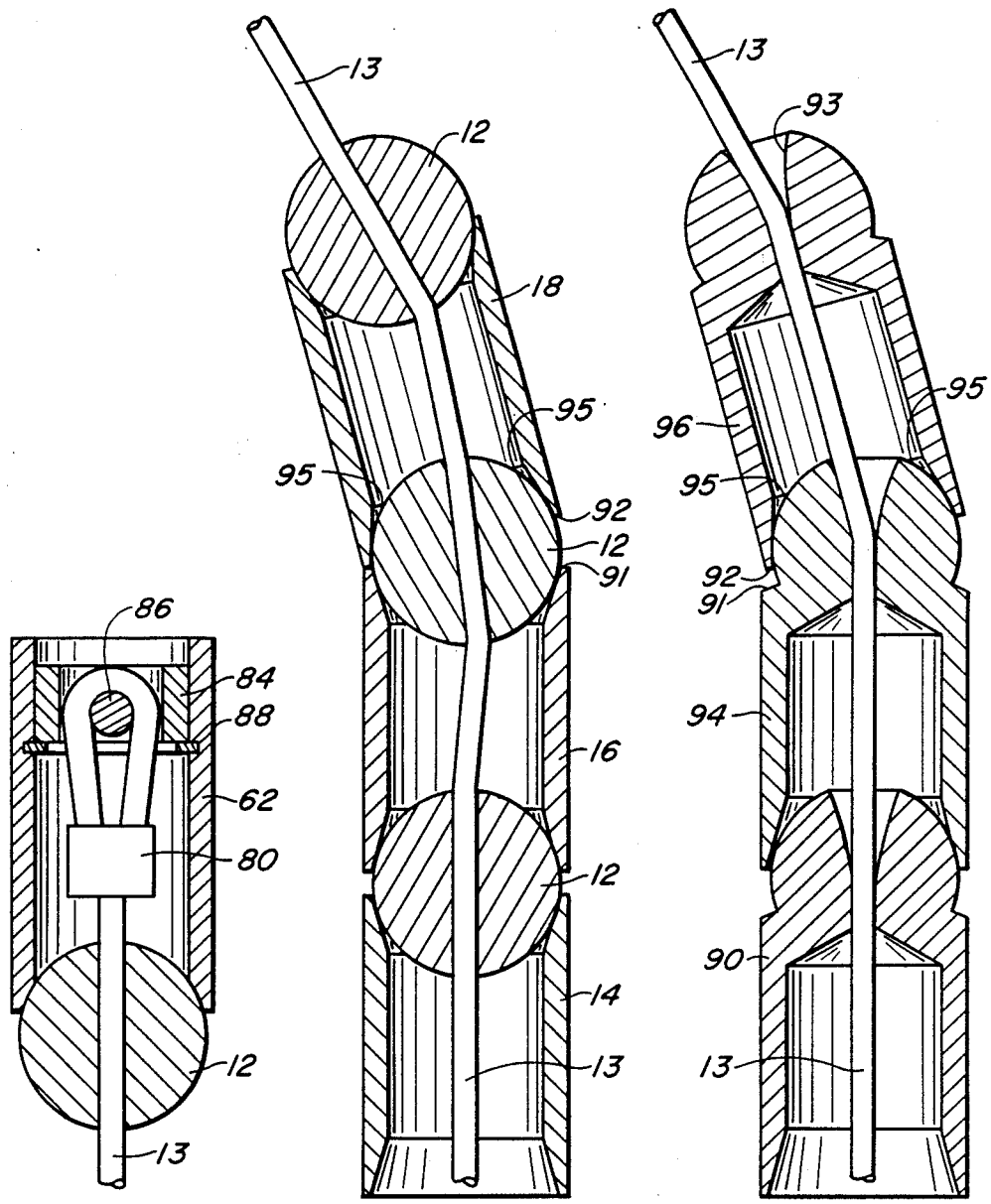
FIG._4.   FIG._5.   FIG._6.

ARTICULABLE COLUMN

BACKGROUND OF THE INVENTION

1. Field of the Invention

This invention relates to articulable columns composed of segmented members held in a set position by friction created and maintained at the member interface by a tensioned means. In particular this invention relates to a method and means for building an improved column of this nature.

2. Description of Prior Art

Articulable columns have long been known for use in positioning micrometers and other measurement tools, or as electric light stands.

U.S. Pat. No. 599,543 discloses a support for incandescent electric lamps where the column is composed of a series of ball/socket members. An extension spring through the column provides tension to lock the column in place. Electrical wires run inside this spring from the base to the lamp fixture.

U.S. Pat. No. 870,429 discloses a sectional stand where a steel cable is used to maintain tension on the ball/socket members. Also a mechanism is provided to increase or decrease tension on the cable.

U.S. Pat. No. 912,308 discloses a sectional stand using alternating bend axis ball/socket members and a detachable means of removing the lamp fixture. Also disclosed is a spirally wound steel cable which forms the tensioned flexible cable. Electrical wires run inside this cable.

U.S. Pat. No. 936,379 discloses an adjustable lamp bracket in which the articulable column is composed of alternating ball and socket members.

U.S. Pat. No. 1,279,803 discloses a light support where a mechanism is provided to readily change tension on an extension spring to increase or decrease stiffness of the column.

U.S. Pat. No. 2,510,198 discloses the use of a flexible positioner as a tool holder. A means is provided to adjust the cable tension. A protective, flexible covering over the column is also shown.

U.S. Pat. No. 3,096,962 discloses a locking device for a measuring apparatus or the like where a single cam mechanism locks both the articulable column and the tool in place.

U.S. Pat. No. 3,529,797 discloses a supporting stand for instruments, primarily surgical instruments, in which the stand can be readily disassembled, sterilized, and reassembled. A wedge mechanism tensions the articulable column cable.

U.S. Pat. No. 3,584,822 discloses a flexible column where the column can be locked or unlocked with a lever at the free end. Electrical wires run alongside a steel tensioning cable inside the column. Means are provided to prevent the column from being twisted.

The disadvantage to prior art columns is that they are not adapted to accommodate the forces acting in the column. Consequently they tend to sag when extended out horizontally to the floor and they are difficult to adjust into new positions.

When an articulable column is held or positioned horizontally to the floor, a large bending moment exists at the base joint of the column from which the full weight of the column and its tool is cantilevered. At the free end, column joints see only a small bending moment due to the free end weight multiplied by a short moment arm. Prior art columns (e.g. 599,543, 936,379, 2,510,198, 3,096,962, 3,168,274, and 3,584,822) built with a stack of identical ball and socket members are not adapted to these varying forces. Because each joint is identical, the stiffness of each joint is the same and therefore under load these columns tend to sag at the base joint where the force is greatest. Adjustment of these columns by gripping the column at the free end is also difficult because, if partially locked, the column remains stiff at the free end while persistently bending at the weakest base joint, or if tension in the column is completely released, the column collapses.

Prior art columns in which the diameter of the ball/socket members is greater at the base than at the free end (e.g. 870,429, 912,308, and 1,279,803) acknowledge the varying forces acting in the column. However for long columns it is an unwieldy and inelegant method and difficult to manufacture.

Accordingly it is an object of this invention to provide an improved method of articulable column construction that overcomes the difficulties of column sag and adjustment.

To accomplish this it is an object of this invention to provide a method for controlling the stiffness at each joint in a segmented articulable column by controlling the friction at each joint interface. By controlling the stiffness of each joint with friction, articulable columns can be built which: (1) are stiff at the base joints where acting forces are large and (2) are relatively flexible at joints near the free end where acting forces are smaller. This allows columns to be built which are slender, articulable, structural members which can support large free end loads, and/or long column lengths. Columns built with this method also can be articulated in a natural, effective fashion.

SUMMARY OF THE INVENTION

In terms of broad inclusion our invention discloses a method of incrementally varying the frictional forces along an articulable column having successive joints formed by alternate ball and socket members. This method is comprised of the following steps: (1) varying the contact angle at selected ball and socket joints at predetermined locations along the column, and (2) applying a compressive force at said selected ball and socket joints.

DESCRIPTION OF DRAWINGS

FIG. 1 is a diagram detailing the forces acting on one ball member of a segmented articulable column.

FIG. 2 is a drawing of one type of segmented articulable column to which the invention can be applied.

FIG. 3 is a sectional view of the base of the articulable column shown in FIG. 2.

FIG. 4 is a sectional view of the free end of the column shown in FIG. 2.

FIG. 5 is a sectional view of one section of ball and socket members in the articulable column shown in FIG. 2.

FIG. 6 is a sectional view of a second column segment type to which the invention can be applied.

DESCRIPTION OF THE PREFERRED EMBODIMENTS

The figures herein and the following description are provided to illustrate a method for varying the friction incrementally along an articulable column. Fundamentally this method relates to the known law that the friction between two bodies held in contact is equal to the force with which the bodies are urged together multiplied by the coefficient of friction between the bodies. The force urging the bodies together is termed the normal force as it exists perpendicular or 'normal' to the contact surface. The coefficient of friction is a unitless proportional constant that represents the experimentally determined relationship between normal force and friction for two contacting materials. Coefficients of friction for many materials and their contact conditions are tabulated in engineering reference books. In the drawings and diagrams herein the application of this law to segmented articulable columns is shown.

To illustrate the method of our invention one type of articulable column is described and shown in FIGS. 1, 2 and 3. This however should not be construed as a limitation to the scope of our invention as we are primarily disclosing a method rather than a specific column design.

FIG. 1 diagrams the forces acting at point P in the circular line of contact between ball member 12 and socket member 18 in reference to the column shown in FIG. 2. The basic concept of our invention is that for a constant cable 13 tension T, the stiffness M of each joint in a segmented column is inversely proportional to the angle A at which the socket member 18 contacts ball 12; where angle A represents the angle between a plane perpendicular to the axis of the column and the ball/socket contact point P, and stiffness M is defined as the resistance to bending in inch-pounds. Joint stiffness relates to angle A because: (1) joint stiffness M is equal to friction F multiplied by the radius of ball member 12, (2) the friction between ball 12 and socket 18 is a function of the normal force N acting perpendicular to the ball 12 surface at contact point P as described in the paragraph above, and (3) Cable tension T is transmitted through the column and is counteracted by normal force N where the normal force N is equal to the tension T divided by the sine of angle A. Adding this up, since joint stiffness M is proportional to friction F and friction force F is proportional to normal force N, changing angle A changes the magnitude of normal force N, the friction F, and results in increasing or decreasing joint Stiffness M. Therefore, by varying the contact angle A over the length of the column, the stiffness of the column joints will vary accordingly.

Table 1 below illustrates the effect of varying the angle A on the normal force N, joint friction F, and joint stiffness M given constant cable tension T for the column joint shown in FIG. 1. As can be seen in Table 1, varying angle A can change the friction F and joint stiffness M by several hundred percent.

TABLE 1

| Angle, A (degree) | Normal Force, N (lbs) N = T/sin(A) | Friction, F (lbs) F = u*N | Joint Stiffness, M (in-lbs) M = F*R | Percent Change (%) |
|---|---|---|---|---|
| 60 | 115.5 | 57.7 | 28.9 | 0 |
| 57 | 119.2 | 59.6 | 29.8 | 3.3 |
| 54 | 123.6 | 61.8 | 30.9 | 7.0 |
| 51 | 128.7 | 64.3 | 32.2 | 11.4 |
| 48 | 134.6 | 67.3 | 33.6 | 16.5 |
| 45 | 141.4 | 70.7 | 35.4 | 22.5 |
| 42 | 149.5 | 74.7 | 37.4 | 29.4 |
| 39 | 158.9 | 79.5 | 39.7 | 37.6 |
| 36 | 170.1 | 85.0 | 42.5 | 47.3 |
| 33 | 183.6 | 91.8 | 45.9 | 59.0 |
| 30 | 200.0 | 100.0 | 50.0 | 73.2 |
| 27 | 220.3 | 110.1 | 55.1 | 90.8 |
| 24 | 245.9 | 122.9 | 61.5 | 112.9 |

TABLE 1-continued

| Angle, A (degree) | Normal Force, N (lbs) N = T/sin(A) | Friction, F (lbs) F = u*N | Joint Stiffness, M (in-lbs) M = F*R | Percent Change (%) |
|---|---|---|---|---|
| 21 | 279.0 | 139.5 | 69.8 | 141.7 |
| 18 | 323.6 | 161.8 | 80.9 | 180.3 |
| 15 | 386.3 | 193.2 | 96.6 | 234.6 |
| 12 | 481.0 | 240.5 | 120.2 | 316.5 | where:
R = 0.5 inches (radius of ball member)
u = 0.5 (coefficient of friction)
T = 100 lbs force (cable 13 tension)
Percent Change = (M at angle A/M at A = 60 degrees) × 100

Using the inverse relationship between contact angle A and joint stiffness M, and incrementally varying angle A at each joint from small values at the column base to larger values at the free end, results in several advantages: (1) long, slender articulable columns can be made which will support substantial free end loads, (2) the columns can be gripped from the free end and reshaped into new positions while supporting the free end load in an easy and natural fashion, (3) tensioning requirements to hold the column in place are reduced making it possible to use lighter duty, simpler, less expensive tensioning mechanisms, and (4) the forces acting on the column can be accommodated without resorting to increasing the diameter of column segments.

The performance of columns with varying friction force joints contrasts sharply to prior art columns in which each joint used the same contact angle A. In prior art columns a large cable tension T was necessary to lock the column in position. This was due to the use of relatively large contact angle A values (typically 28 degrees.) Using such a large angle A reduced the normal force N acting at the ball/socket interface for a given tension T. Therefore to create sufficient normal force and thus joint stiffness at the base joints where the cantilevered load of the column was greatest, a large cable tension was necessary. Toward the free end, since all the joints had the same contact angle A, the joints were as stiff as the base joints though the acting forces were much smaller. Consequently prior art columns were difficult to bend into new shapes when gripped from the free end. If this was attempted, the column simply bent at the base joints where the bending force was greatest. To reshape these columns, tension had to be released which caused the column to collapse.

Some prior art columns varied the size of the ball diameter over the length of the column using larger diameter balls at the base joints where bending moments on the joints were greatest. Increasing the diameter of the joint increased joint stiffness because as stated above stiffness is equal to friction at the ball/socket interface multiplied by the ball radius. In these columns the joint friction was constant and the ball radius was changed to change the stiffness. Table 2 below contrasts our method of varying friction with this method of varying ball diameter. In Table 2, the equivalent ball diameter represents the ball diameter needed to make a joint as stiff as the value achieved by using our method of changing the friction by changing angle A. The contact angle 28 degrees was used to calculate friction for the equivalent diameter calculations because it appears to be a typical contact angle value for prior art articulable columns (as scaled off the patent drawings.)

TABLE 2

| Angle, A (degrees) | Joint Stiffness, M (inch-lbs) | Equivalent Diameter, D (inches) |
| --- | --- | --- |
| 60 | 28.9 | 0.54 |
| 57 | 29.8 | 0.56 |
| 54 | 30.9 | 0.58 |
| 51 | 32.2 | 0.60 |
| 48 | 33.6 | 0.63 |
| 45 | 35.4 | 0.66 |
| 42 | 37.4 | 0.70 |
| 39 | 39.7 | 0.75 |
| 36 | 42.5 | 0.80 |
| 33 | 45.9 | 0.86 |
| 30 | 50.0 | 0.94 |
| 27 | 55.1 | 1.03 |
| 24 | 61.5 | 1.15 |
| 21 | 69.8 | 1.31 |
| 18 | 80.9 | 1.52 |
| 15 | 96.6 | 1.81 |
| 12 | 120.2 | 2.26 | where:
Angle A represents contact angle values from Table 1.
Joint Stiffness M values are taken from Table 1 and represent the joint stiffness that results from using the corresponding angle A.
Equivalent Diameter D is the ball member diameter and is described by the formula: $D = 2 * (M/F(28))$. Where $F(28)$ equals the ball/socket friction for a contact angle of 28 degrees, using cable 13 tension T and coefficient of friction u values taken from Table 1.

Looking at Table 2 it can be seen that while changing the ball diameter to counteract column forces is a viable method, there are disadvantages: (1) it is difficult and expensive to manufacture the variety of ball and socket sizes needed, and (2) it is bulky and inelegant compared to slender constant diameter columns. These disadvantages notwithstanding, there may be uses for an articulable column design which combines the methods of varying friction and ball diameter to accommodate the varying forces in a column.

FIG. 2 is a drawing of a segmented articulable column to which the method of our invention has been applied. The column is composed of alternating ball and tubular socket members held in a set position by an internal tensioned cable. Socket 64 is the base or first socket member. Ball member 12 rests in socket 64 and socket member 10 rests on ball 12. This pattern of alternating ball and socket members continues up the length of the column. Socket members are given distinct numbers because each has a different bevel angle B as shown in FIG. 1 such that contact angle A is different on each ball member. By varying the bevel angle B of each socket member, the stiffness of each joint can be controlled. For example, joints near the base (joints between sockets 64, 10, 14, and 16) have a small bevel angle B and therefore are stiff and tend to counteract the large cantilevered load of the column. Joints near the free end (joints between sockets 56, 58 and 60) have a larger bevel angle B so that they are appropriately less stiff accommodating only the relatively small bending moment forces. At the column base, base tube 66 houses a cable tensioning assembly of which knob 68 is used to increase or decrease cable tension. Clamp 70 is secured to the base socket 64 and serves to fix the column base to a stationary surface. At the column free end, top socket 62 secures the internal tensioned cable and threaded holes are provided to mount load 63 which can be tools, light fixtures, or any other device.

FIG. 3 is a sectional view of the base of the articulable column shown in FIG. 2. Ball 12 rests between base socket 64 and socket 10 and forms the first joint in the column. Tensioning cable 13 ends in a loop held with crimp nut 82. This loop fits over the eye of extension spring 73. Slide 72 is welded to extension spring 73. Screw 74 is secured in slide 72 and fits in a slot 66A machined in base tube 66. Threaded rod 76 screws into slide 72 and is permanently locked in knob 68 with jam nut 77. Bearing 78 fits into a groove in knob 68 and base tube 66 rests on this bearing. Tension on the cable 13 is increased when the knob 68 is turned clockwise turning threaded rod 76. Slide 72 is pulled down by thread engagement with rod 76 pulling down extension spring 73 and cable 13. The slide 72 is prevented from rotating when the threaded rod is turned by screw 74 engaged in slot 66A in tube 66. Extension spring 73 serves to maintain cable 13 tension when the column is bent into new shapes which causes the cable effective length to change. Base socket 64 is counterbored to fit on base tube 66. Screws 71 attach clamp 70 to the column.

FIG. 4 is a sectional view of the free end socket assembly. The free end socket 62 has provisions for securing cable 13 and tool attachments to top socket 62. Cable 13 ends in a loop held with crimp lug 80. Bolt 86 passes through the loop and is threaded into end piece 84. End piece 84 abuts against internal retaining ring 88 when the cable in tensioned.

FIG. 5 is a sectional view of several joints in the column shown in FIG. 2. Socket 14 supports ball 12 upon which socket 16, ball 12 and socket 18 are respectively disposed. Tensioning cable 13 passes through a center aperture in the assembly. The shoulder 91 of socket 16 and the shoulder 92 of socket 18 are made to butt against each other to limit the maximum bend angle of the joint. The shoulders of all socket members in the column are designed in this fashion. The angle of bevel 95 of each socket is different and depends upon the position of each socket in the column. At the base joints, small angles are used creating a large wedging force between socket 64, ball 12 and socket 12 thus creating a stiff joint (in reference to FIG. 2.) Larger angles are used at the free end joints. It can be noted here that in long columns the joint bevel angles near the free end are not critical as long as they support the free end load and allow for easy column articulation. This is because the forces acting on the column are relatively small and most forces are due to the user reshaping the column by gripping it from the free end. In the column shown in FIG. 2, sockets 48 through 62 use the same bevel 95 angle.

An alternate ball/socket segment embodiment is shown in FIG. 6. In this configuration the ball and socket are formed into unitary member 90. The opening in the top of the ball 93 is tapered to decrease changes in the effective length of tensioned cable 13 when the column is bent. The angle of bevel 95 of the socket is varied over the length of the column as described above. Socket shoulders 91 and 92 are used to limit the maximum bend of each joint as described in FIG. 5.

Thus the reader will see that the method of the present invention provides an improvement in articulable columns which can have many applications. While our above descriptions contain many specificities, these should not be construed as limitations on the scope of the invention, but rather as an exemplification of preferred embodiments thereof. Many other variations are possible. For example, skilled artisans will readily be able to change the dimensions and shapes of the various embodiments. They can arrange stiff and flexible joints within the column as needed to suit their application. One example of this would be to use our invention to dampen the vibrations of a tensioned cable. In this application, stiff joints could be positioned at areas of large vibration amplitudes while flexible joints could be used at the node areas of the cable. Skilled artisans will also be able to make the column of alternative materials such as plastics. They can make many variations on the tensioned means and tensioning mechanism. They can make various column mounting arrangements and affix tools, fixtures or lamps to the column free end. Accordingly, the scope of our invention should be determined not by the embodiments illustrated, but by the appended claims and their legal equivalents.

We claim:

1. The method of varying by incrementally different amounts the frictional engagement forces simultaneously applied along an articulable column having successive joints formed by alternate ball and socket members arranged along an elongated central axis, comprising the steps of:
   (a) applying a compressive force at said ball and socket joints where said compressive force is applied in the direction of said elongated central axis of the column;
   (b) varying by different incremental amounts the ball/socket contact angle defined by a plane perpendicular to the column axis and including the center of the ball and a line including said contact point of said ball and socket and said ball center, whereby incorporation of different contact angles at selected ball and socket joints varies said frictional forces at each joint responding to the formula:

$$F = (T^*u)/\mathrm{SIN}\,(A)$$

where F=the frictional force at said joint, T=the applied compressive force, u=the coefficient of friction of the materials in contact, and A=the contact angle.

2. An articulable column having an elongated central axis, comprising:
   (a) a series of ball and socket members arranged along said central axis to form articulable ball and socket joints frictionally engaged over the length of the column, said ball member having a center common to the frictional surface thereof and an aperture therethrough coincident with said column axis; and
   (b) means generatively associated with said ball and socket members retaining said ball and socket members in frictional engagement;
   (c) said socket members comprising a cradle having surfaces contiguously receiving said ball members at a contact angle defined by a plane perpendicular to the column axis and including said ball center and a line including the contact point of said socket member on said ball member and including said center;
   (d) said contact angle of a first ball and socket joint comprising a first predetermined value;
   (e) said contact angle of a second ball and socket joint comprising a second predetermined value larger than or smaller than said contact angle of said first ball and socket joint;
   (f) whereby the first and second predetermined values of contact angles for the first and second ball and socket joints provide incrementally varying frictional forces in said series of ball and socket joints over the length of the column.

3. An articulable column according to claim 2, wherein said ball members are provided with spherical frictional surfaces and said socket members are tubular having distal ends formed with conically beveled frictional surfaces contacting the spherical frictional surfaces of said ball members.

4. An articulable column according to claim 3, wherein means are provided on said tubular socket members and associated with said spherical frictional surfaces of said ball members to limit the bend angle of individual joints in the column.

5. An articulable column according to claim 2, wherein said ball and socket members constitute unitary ball/socket column segments comprising a ball end having a spherical frictional surface and a distal tubular socket end having a conically beveled surface to receive the ball end of an adjoining said ball/socket member.

6. An articulable column according to claim 5, wherein each said tubular socket end of each said unitary ball/socket member projects around the ball end of the adjoining ball/socket member and cooperates with a circular shoulder on said ball end to limit the bend angle of individual joints in the column.

7. An articulable column according to claim 2, wherein said means generatively associated with said ball and socket members retaining said ball and socket members in frictional engagement comprises a cable extending longitudinally through the center apertures in said ball and socket members, means anchoring said cable to one end of the column, and means operatively associated with the opposite end of the column manipulable to tension said cable to exert a compressive force on said column members.

8. An articulable column according to claim 7, wherein said cable tensioning means comprises:
   (a) means including an extension spring member comprising a means of securing said cable at one end and a threaded nut attached to the opposite end;
   (b) a rod threaded into said threaded nut and extending into said extension spring;
   (c) handwheel means to turn said threaded rod permanently attached to said rod; and
   (d) means preventing said extension spring member from rotating in relation to said articulable column;
   (e) whereby tension to lock the column in a selected configuration is applied to said cable by turning said handwheel so as to draw said extension spring member toward said handwheel.

* * * * *